(12) United States Patent
Laguette et al.

(10) Patent No.: US 6,739,722 B2
(45) Date of Patent: May 25, 2004

(54) APPARATUS AND METHODS FOR MEASURING ACCOMMODATION OF A LENS IN AN EYE

(75) Inventors: Stephen W. Laguette, Santa Barbara, CA (US); Alan J. Lang, Long Beach, CA (US); Alan Schier, La Canada, CA (US); Joseph Warren Asa, Gendora, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 28 days.

(21) Appl. No.: 10/234,592

(22) Filed: Sep. 4, 2002

(65) Prior Publication Data

US 2004/0041980 A1 Mar. 4, 2004

(51) Int. Cl.⁷ .................................................. A61B 3/02
(52) U.S. Cl. ...................................................... 351/243
(58) Field of Search ................................ 351/205, 206, 351/208, 211, 210, 216, 221, 233, 236, 237, 242, 243, 246

(56) References Cited

U.S. PATENT DOCUMENTS

| 4,105,302 A | * | 8/1978 | Tate, Jr. ........................ 351/210 |
| 4,408,846 A | | 10/1983 | Balliet |
| 4,533,221 A | | 8/1985 | Trachtman |
| 4,660,945 A | | 4/1987 | Trachtman |
| 4,778,268 A | | 10/1988 | Randle |
| 4,838,677 A | | 6/1989 | Bronskill et al. |
| 4,943,151 A | | 7/1990 | Cushman |
| 5,223,866 A | | 6/1993 | Cushman |
| 5,374,193 A | | 12/1994 | Trachtman |
| 5,450,145 A | | 9/1995 | Valentine |
| 5,828,439 A | * | 10/1998 | Ueno ........................... 351/205 |
| 6,033,073 A | | 3/2000 | Potapova et al. |
| 6,249,589 B1 | | 6/2001 | Hoch |
| 6,382,795 B1 | | 5/2002 | Lai |
| 6,575,572 B2 | * | 6/2003 | Lai et al. ...................... 351/211 |

* cited by examiner

*Primary Examiner*—George Manuel
(74) *Attorney, Agent, or Firm*—Peter Jon Gluck; Anthony G. Vella

(57) ABSTRACT

Apparatus for measuring accommodation of a lens in an eye includes a target, a Badal lens, and a viewing aperture, where the Badal lens and the viewing aperture are positioned so that when the target moves towards or away from the lens, the apparent size of the target remains constant to a subject looking in the viewing aperture regardless of the distance the target moves. The apparatus may be provided in a compact housing and may include a mirror placed in the housing so that the viewing aperture can be placed away from the optical axis of the lens. The apparatus includes a controller to control the movement of the target. The apparatus measures the accommodation of a lens based on the distance the target moves during an examination. Methods of measuring accommodation of a lens in an eye of a subject are also disclosed.

28 Claims, 4 Drawing Sheets

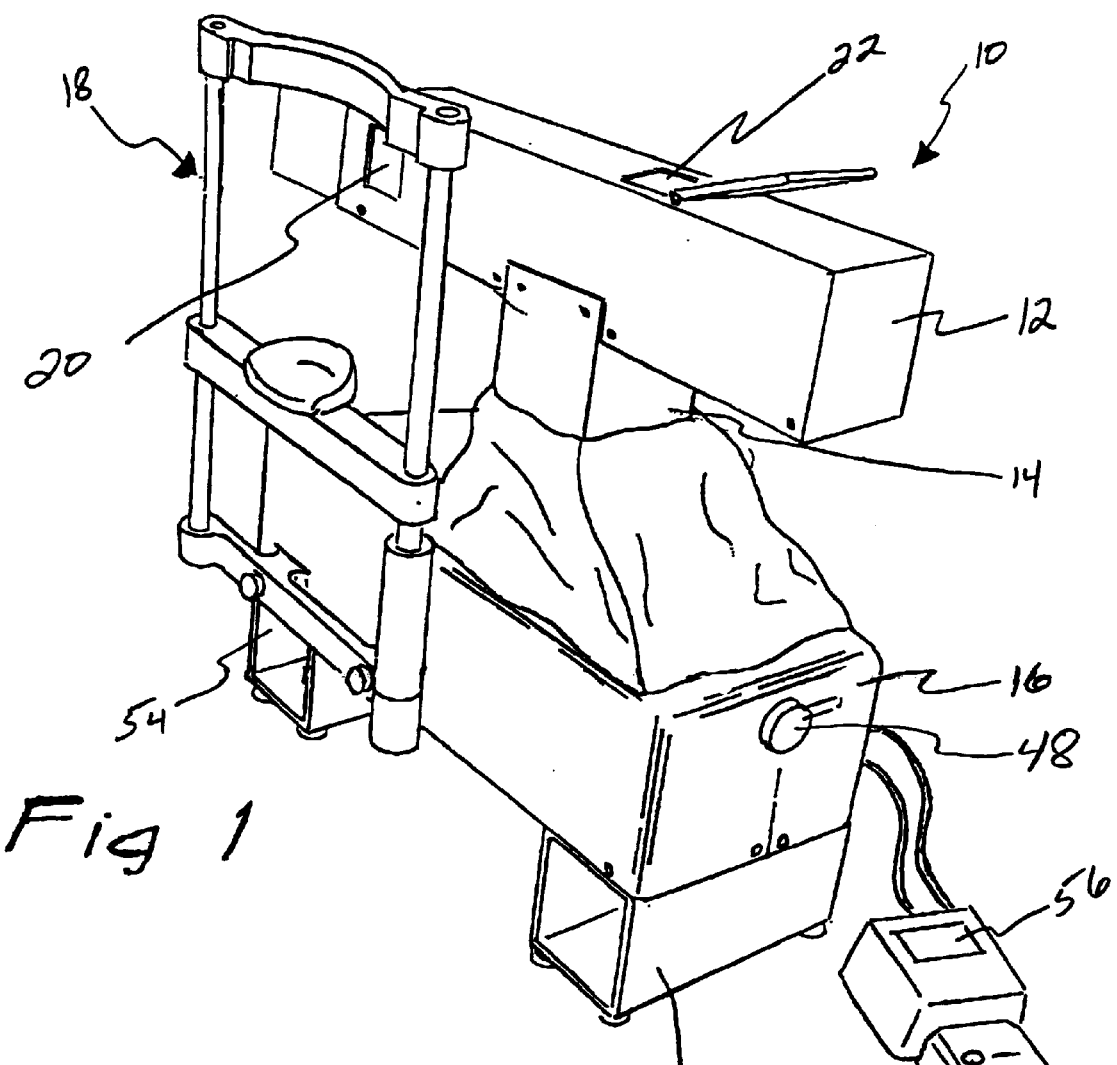
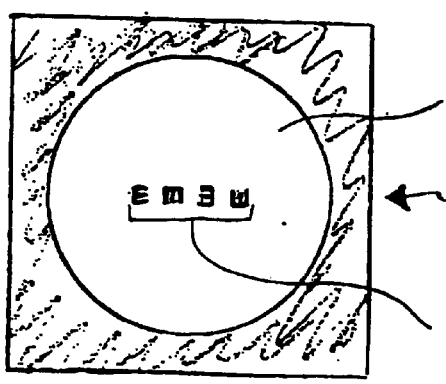

APPARATUS AND METHODS FOR MEASURING ACCOMMODATION OF A LENS IN AN EYE

BACKGROUND OF THE INVENTION

1. Field of the Invention

The invention disclosed herein relates to ophthalmic instruments and methods, and more particularly, relates to apparatus and methods for measuring accommodation of a lens in an eye.

2. Description of Related Art

Accommodation is the adjustment of an eye for seeing objects at different distances. Accommodation is accomplished by changes in the curvature of a lens in an eye.

Typically, accommodation is measured in a subject by asking a subject to hold a letter chart in one of his hands. The letter chart has multiple rows of letters decreasing in size from one end of the chart to the other end of the chart (i.e., top to bottom). The subject is asked to close one eye, and to focus on one of the rows of letters. The subject is then asked to bring move the letter chart closer to his eye and to stop moving the chart when the row of letters becomes blurred. The process may be repeated several times to provide an average value. The distance which the chart is moved from a focused position to a blurred position may then be used to determine the amount of accommodation of the subject's eye. However, this method suffers from several shortcomings including that the accuracy of hand movements of the letter chart is not very accurate and repeatable, and that the size of the rows of letters increases as the letter chart moves closer to the eye. The change in size of the letters confounds the test, and results in inaccurate measurements of accommodation.

U.S. Pat. No. 4,778,268 (the '268 patent) discloses a testing system that measures accommodation of a subject's eye. The system is relatively complicated and awkward to use. The system includes an illumination source, a target with a small light transmitting portion and a large light blocking portion, and multiple lenses between a viewing aperture and the target. The system also uses a manually operated movement assembly to move the target and illumination source along a track. The particular configuration disclosed in the '268 patent is necessary to create a virtual image that is viewed by the subject, and to provide the visual training capabilities of the system. The system of the '268 patent suffers from its necessarily complex design and the inaccuracies associated with manual control of the system.

SUMMARY OF THE INVENTION

The present invention addresses the shortcomings of current techniques and systems.

An apparatus, as disclosed herein, for measuring accommodation of a lens in an eye provides consistent, controlled, and repeatable presentations of a fixed accommodative stimulus to a subject, such as a person. The apparatus determines the amplitude of accommodation based on the equivalent dioptric change of a target of the apparatus that is viewed by the subject. By making use of the Badal principle, the apparent size of the stimulus remains substantially constant at all optical distances. Thus, the subject viewing the target receives the same stimulus in terms of spatial frequencies at all distances. The constancy of the stimulus helps to improve the repeatability of the accommodative amplitude measurements.

An apparatus for measuring accommodation of a lens in an eye may have a housing; a viewing target located in the housing and located on a track that permits the target to move in the housing; a viewing aperture located in the housing to permit the subject to view the target; and a lens located between the target and the viewing aperture at a position that provides a substantially constant apparent size of the target when viewed by the subject regardless of the distance between the target and the viewing aperture.

An apparatus for measuring accommodation of a lens in an eye of a subject may also have a viewing aperture; a physical target positioned on a track so that the target can move along the track toward or away from an eye of a subject viewing the target through the viewing aperture; and a lens located in the apparatus so that when the physical target is viewed by the subject through the viewing aperture, the lens is positioned between the target and the subject's eye, and the target has a substantially constant apparent size regardless of the distance between the target and the viewing aperture.

In addition, an apparatus for measuring accommodation of a lens in an eye of a subject may include a target located in the apparatus and moveable towards or away from an eye of a subject when the subject is viewing the target, the target being structured to maintain a substantially constant pupil size of the eye as the target is moved towards or away from the eye.

Methods of measuring accommodation of a lens in an eye of a subject include steps of moving a viewable target from a first position to a second position, monitoring the distance between the first position and the second position, and determining the accommodative amplitude based on the distance. The methods may be performed by a subject who is viewing the target, and may be performed without any assistance by another person.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description.

BRIEF DESCRIPTION OF THE FIGURES

FIG. 1 is a front perspective view of an apparatus for measuring accommodation of a lens in an eye.

FIG. 6 is a view of an image of a target in the apparatus of FIG. 1.

DETAILED DESCRIPTION

Figure 2:
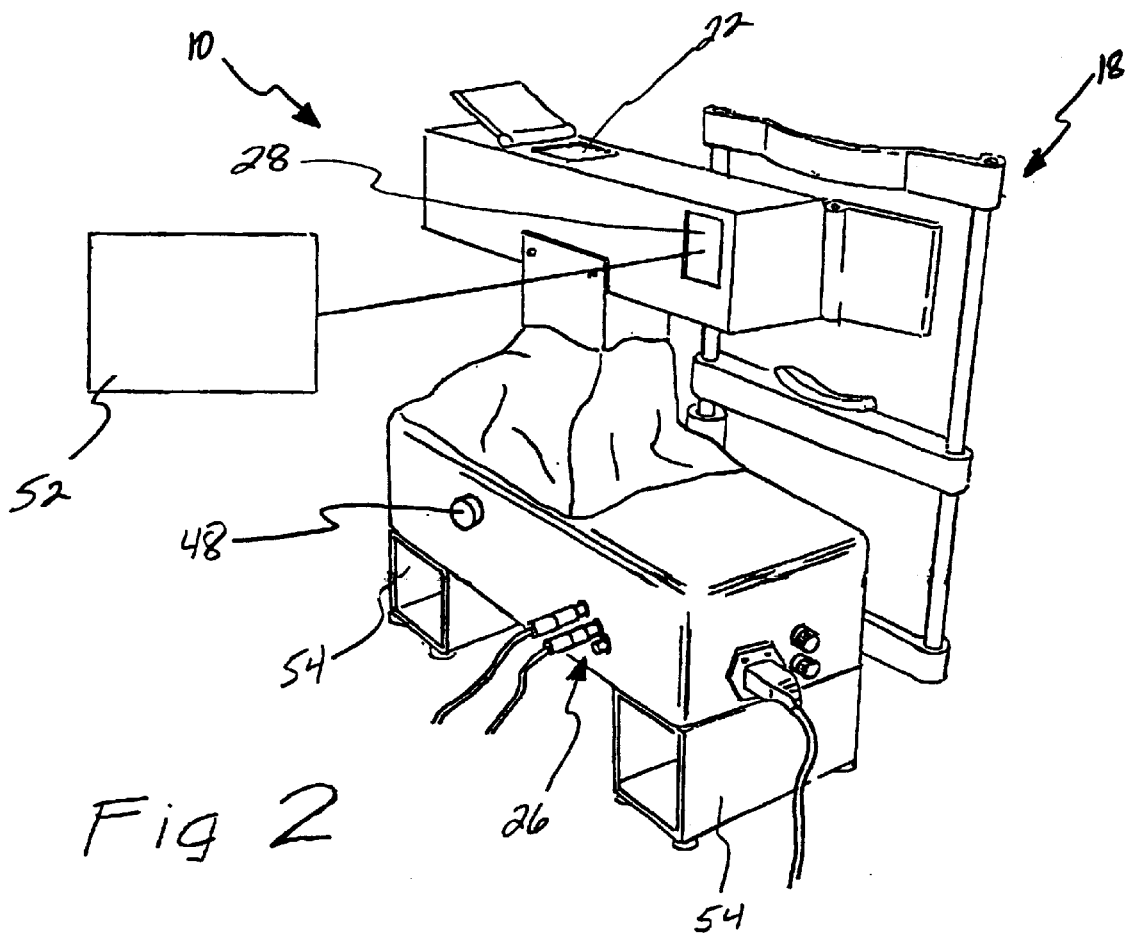
FIG. 2 is a rear perspective view of the apparatus of FIG. 1.

As illustrated in FIGS. 1 and 2, an apparatus 10 for measuring accommodation of a lens in an eye has a housing 12, a support structure 14, and a base 16. Apparatus 10 is a self-contained apparatus that is compact and easily useable. For example, apparatus 10 is sized to fit on relatively small surfaces, such as a table top or the like. One or more spacers 54 may be provided to adjust the height of apparatus 10. As disclosed herein, apparatus 10 may be used to determine the accommodation of any lens in an eye, including natural lenses, and implanted intraocular lenses. Because of its relatively compact size and its ease of use, apparatus 10 may be used in clinical settings, such as physician's offices or medical clinics, or may be used in businesses that are not necessarily medical businesses. For example, the apparatus may provide a convenient way for consumers to test their vision while they are at a store. Among other things, providing consumer self-tests should provide a substantial improvement of preventative medicine regarding the eye, and should reduce costs associated with preventative medicine.

Apparatus 10 is illustrated as having a fixation device 18 that is structured and positioned with respect to apparatus 10 to maintain a subject's eye in a relatively fixed position, as described herein. Fixation device 18 is illustrated as having a chin rest, and a forehead rest, and a frame that is attached to base 16. However, other fixation devices may only have a chin rest, a forehead rest, or other similar structure that maintains a fixed position of the subject's head while the subject is performing the procedure of measuring accommodation of a lens in his eye.

Apparatus 10 also includes one or more adjustment devices 48 which control the coarse positioning of a viewing aperture 20 in housing 12. In the illustrated apparatus, three adjustment devices are provided, one for controlling vertical position, one for controlling horizontal position parallel to the length of apparatus 10, and one for controlling horizontal position perpendicular to the length of apparatus 10. The illustrated adjustment devices 48 are knobs that can be rotated to adjust the position of viewing aperture 20 with respect to the position of fixation device 18.

Housing 12 of apparatus 10 is illustrated as having a plurality of apertures opening into the housing. For example, a viewing aperture 20 is provided to permit a subject to view a target located in housing 12, as discussed herein; a target access aperture 22 is provided to permit access to the target in the housing; and a instrument aperture 28 is provided to permit one or more additional instruments to be operably connected to apparatus 10 to make measurements of the subject's eye. Although the apertures are illustrated in relatively particular positions, the apertures may be provided in different positions and/or orientations. For example, in apparatus of the invention that do not utilize a mirror, viewing aperture 20 may be provided along the central optical axis of the lens, discussed herein, to provide a linear view of the target by the subject. In addition, target access aperture can be provided at any position along housing 20 to permit a user to access and physically manipulate the target located in the housing. Additionally, instrumentation aperture 28 can be omitted if desired.

Apparatus 10 is also shown as including at least one controller 24 that controls the operation of apparatus 10. Controller 24 includes one or more controller keys 46, and a display 56, such as a liquid crystal display (LCD). Controller 24 is in communication or is operably coupled with apparatus 10 via one or more cables that connect to one or more controller ports 26, as shown in FIG. 2. Any conventional cables and ports may be used. In the illustrated apparatus, controller ports 26 are BNC connectors. Apparatus 10 may include a plurality of controllers 24. For example, one controller may be provided that controls parameters such as target brightness, target speed, and the like, and a second controller may be provided that starts and stops the target from moving. Either, or both, controllers may be sized to fit within a person's hand so that either controller may be held by the subject viewing the target.

Apparatus 10 is provided with a computer that measures the accommodation amplitude of a lens in an eye of a subject. The computer may be provided in controller 24, or may be provided in housing 12, support structure 14, or base 16. In the illustrated embodiment of apparatus 10, a computer is provided in controller 24. Using one or more controller keys 46, a user can access multiple menus and select desired operations or parameters for testing. For example, the user can calibrate the apparatus, can reset the "near" position of the target so that the target returns to the closest stimulus position (e.g., the high diopter setting); can reset the "far" position of the target so that the target returns to the farthest stimulus position (e.g., the low diopter setting), can start and/or stop the movement of the target; can control the brightness of the target, the rate at which the target moves, and any offset of the stimulus. The computer can monitor the distance that the target moves, and determine the accommodative amplitude based on the distance, as discussed herein.

Figure 3:
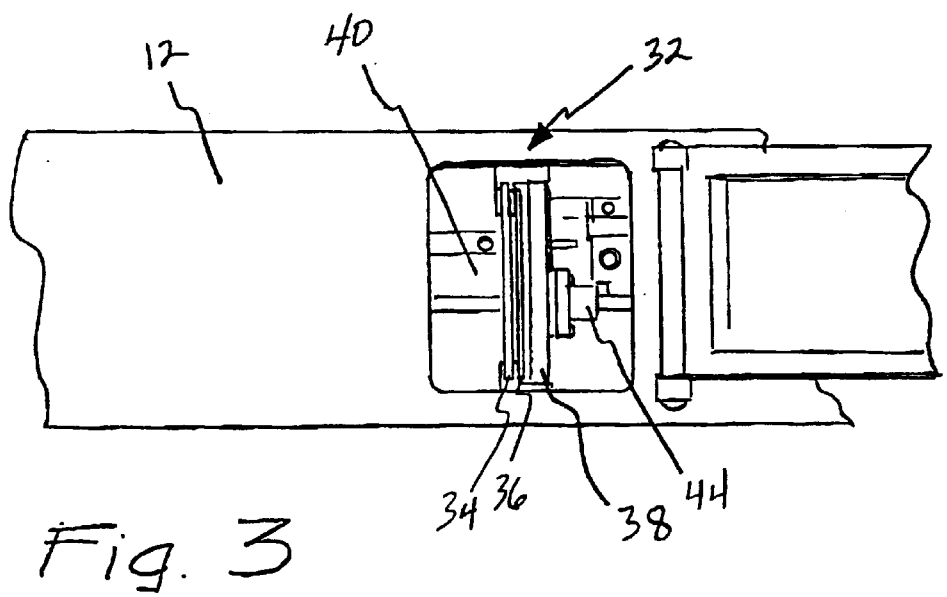
FIG. 3 is a top plan view of a viewable target of the apparatus of FIG. 1.
Figure 3A:
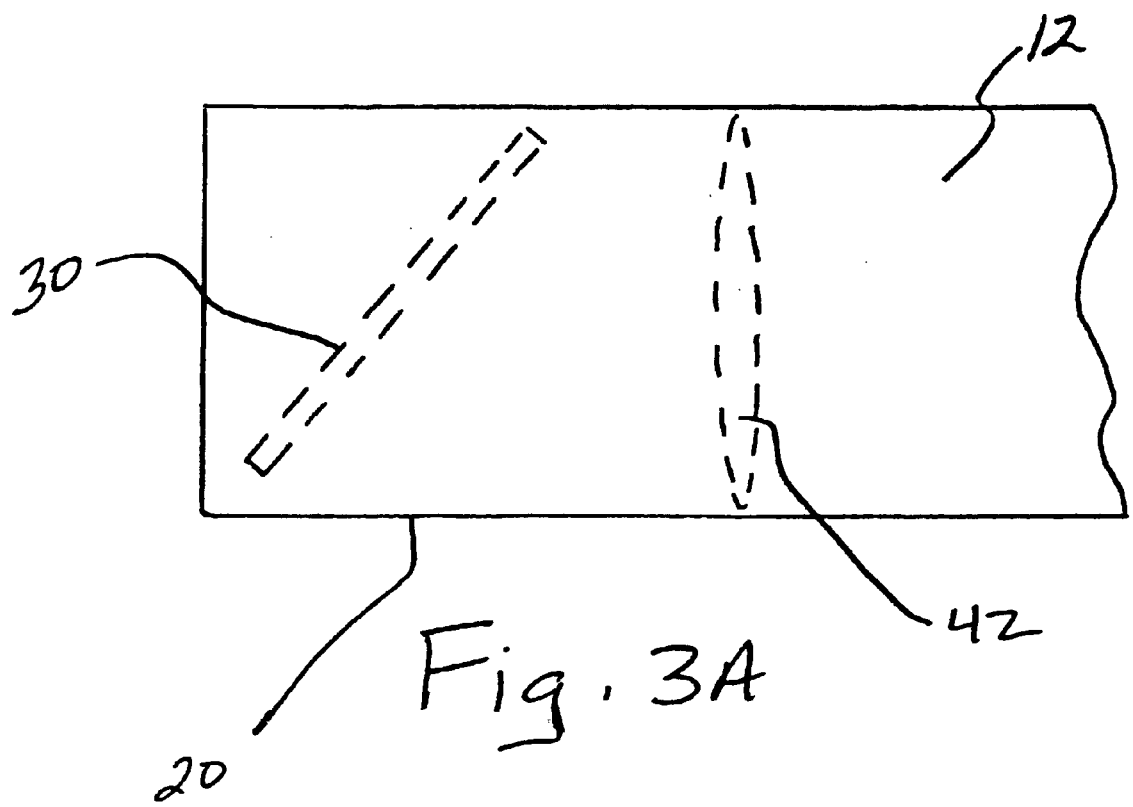
FIG. 3A is a top plan view of the housing of the apparatus of FIG. 1 illustrating the general position of a mirror and a lens.

FIGS. 3 and 3A illustrate elements of apparatus 10 provided in housing 12. As shown in FIG. 3, a target 32 is illustrated as being located on a track 40. Track 40 extends along the length of housing 12 so that target 32 can move within housing 12 towards two ends of housing 12. Track 40 may have a plurality of increments that allow target 32 to incrementally move along track 40. In the illustrated apparatus, track 40 includes a threaded rod; however, in other apparatus, track 40 may include a plurality of notches disposed along the length of the track, or may include one or more switches that provide starting and stopping points of target 32 as it moves along track 40.

Target 32 is illustrated as having an image 34, a translucent member 36, and an illumination source 38. Target 32 is coupled to a drive mechanism 44, which causes target 32 to move along track 40. Drive mechanism 44 is operative coupled to a computer, as described above. Image 34 is illustrated as being a slide, such as a 35 mm slide used in conventional photography. Translucent member 36 is illustrated as a white sheet located between image 34 and illumination source 38. Illumination source 38 is illustrated as a lighted panel, for example, a panel having a plurality of light emitting diodes (LEDs). Illumination source 38 provides a substantially uniform level of light, such as white light, that is transmitted through translucent member 36 and image 34. Translucent member 36 is structured to permit light to pass through the background, thus, translucent member is also understood to be a light transmitting member. Translucent member 36 preferably is not transparent.

Image 34 is a physical object, such as a 35 mm slide, and contains an opaque region or opaque portion (e.g., a region that does not permit light to pass therethrough), and a non-opaque region or portion (e.g., a region that allows light to pass therethrough). The opaque region occupies a minor portion of the area of the image, or the target, and the non-opaque region occupies a major portion of the area of the image, or target. As used herein, the term "minor portion" refers to less than 50%. In one embodiment, the opaque region is less than 20% of the area of the image, and in another embodiment, the opaque region is less than 10% of the area of the image. Thus, target 32 includes an image that is disposed on a light-colored background. In one embodiment, the light-colored background is white. Providing an opaque region that occupies less than 50% of the area of the image facilitates controlling the dilation of the pupil of the subject's eye. Target 32 is configured so that the dilation of the pupil of the subject's eye is substantially constant during the test procedure. Maintaining a relatively constant pupil size is achieved by providing a target having a relatively large bright background, which causes the pupil to contract. The brightness of the target can be controlled to provide the desired amount of pupil contraction or dilation for the particular subject being tested. In addition, the brightness of the target can be controlled to provide the desired amount of pupil dilation for a particular age range of subjects. Thus, the results obtained with apparatus 10 may be standardized across a population of individuals by reducing variability of pupil dilation associated with different age groups of people. Although target 32 is illustrated as an assembly having an LED panel, a translucent member, and an image, target 32 may be an LCD screen capable of displaying different images, such as an LCD screen associated with video recorders. Furthermore, target 32 may also include an illumination source that is structured to provide relatively even level of brightness and thereby eliminating the need for a separate translucent background.

Figure 4:
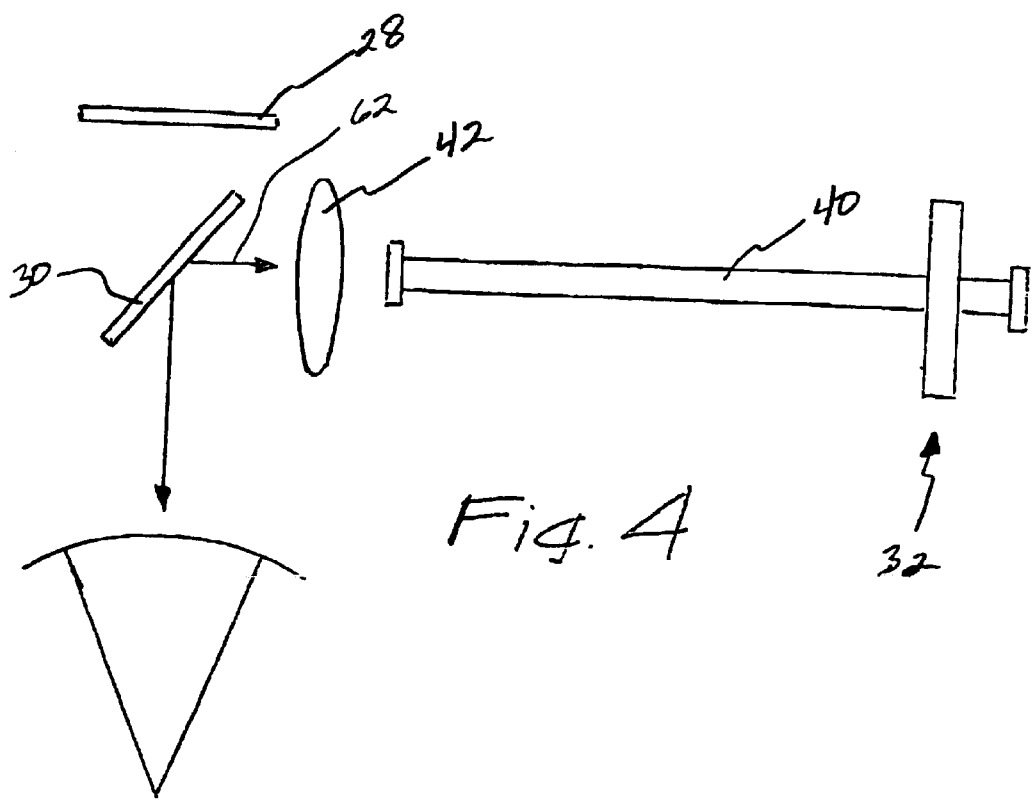
FIG. 4 is a schematic diagram of the apparatus of FIG. 1.
Figure 5:
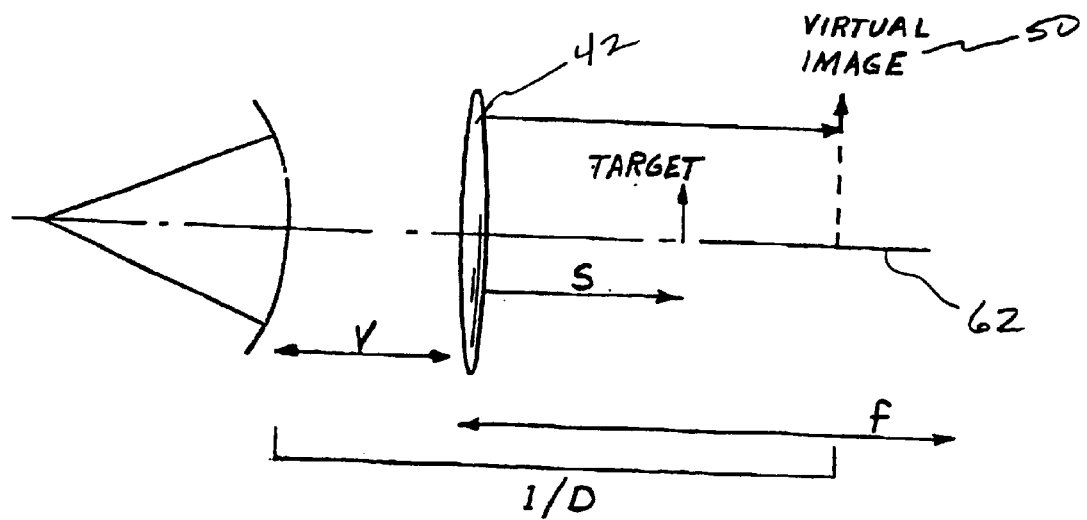
FIG. 5 is a schematic diagram of some features used in measuring accommodation of a lens.

FIG. 3A illustrates the general positions of a lens 42 and a mirror 30 located in housing 12. As illustrated, lens 42 is positioned between viewing aperture 20 and target 32. Lens 42 is structured to maintain a substantially constant image size of the target image 34 as target 32 moves along track 40. Lens 42 is a Badal lens. Thus, apparatus 10, in contrast to the system disclosed in U.S. Pat. No. 4,778,268, includes a single lens disposed between the viewing aperture 20 and target 32. Mirror 30 is positioned in proximity to viewing aperture 20 to enable a subject to view an image of target image 34 as it reflects off of mirror 30. Mirror 30 is oriented in housing 12 so that the subject can view target image 34 when the subject is not viewing the target image 34 along the optical axis 62 (as shown in FIGS. 4 and 5) of lens 42. In other words, mirror 30 is oriented so that a subject may view target image 34 at an approximately ninety degree angle with respect to optical axis 62 of lens 42. In the illustrated embodiment, mirror 30 is oriented at approximately forty-five degrees with respect to the length of housing 12 or central optical axis 62.

FIG. 5 illustrates various parameters used in measuring the accommodation of a lens in a subject's eye. In reference to FIG. 5, "s" is the target; "D" is the equivalent stimulus diopter; "f" is the focal length of the lens; "v" is the vertex distance. If v=f, the Badal condition is obtained, and D is linearly related to the target location. This can be demonstrated by the following equation (Equation I):

$$fD=(1-s/f)$$

Equation I is programmed into a computer provided with apparatus 10. Details of the Badal principle are well known, and can be found in "The Eye and Visual Optical Instruments", Smith and Atchinson, Cambridge University Press, chapter 30, 1997, which is incorporated by reference herein.

FIG. 6 illustrates a virtual image 50 as seen by a subject looking through viewing aperture 20. Virtual image 50 has an opaque region 58 and a non-opaque region 60. As discussed hereinabove, opaque region 58 occupies a minor portion of the area of the image, and the non-opaque region occupies a major portion of the area of the image. This relationship contributes to the apparatus' ability to maintain a relatively constant pupil size of the subject when he is viewing the image. The opaque region of target image 34 should be relatively simple, and sharp to permit a subject to reliably determine when the image begins to blur or become focused.

A computer of apparatus 10 is generally pre-programmed to measure the equivalent of either positive-relative or negative relative accommodation amplitudes. The computer may be operated by pressing any number of keys 46 provided on controller 24, as discussed above. The keys cause a menu, with one or more submenus, to be displayed on display 56. Instructions for performing the test may also be displayed on the display. The user of apparatus 10 can select either test, or a combination of tests. An operator, which may be the subject taking the test, begins a test when the image is in focus by pressing a key 46 that starts the test. The subject may then press a key 46 to stop the test when the image viewed by the subject begins to blur. This test is the positive-relative test. In a negative-relative test, the image is first blurred when the scan is started, and the subject presses a stop key when the image becomes focused. The computer may then determine the accommodative amplitude in diopters based on the distance the target moved from the start of the test to the end of the test. The accommodative amplitude is the reciprocal of the distance the target moved. It is preferable for the subject to repeat the tests multiple times using the same criteria for blurred and focused images to provide an average with consistent results. With the apparatus disclosed herein, the measurement error is low, for example, the error is typically less than 0.25 diopters with a three diopter stimulus. Lower errors (e.g., errors lower than 0.20 diopters, and lower than 0.10 diopters) are also obtainable with the apparatus.

Accordingly, a method for measuring accommodation of a lens, including implanted intraocular lenses, in an eye of a subject includes the steps of moving a target, which is structured to maintain a relatively constant pupil size in an eye of the subject viewing the target, from a first position towards or away from the subject's eye to a second position; determining the distance between the first position and the second position; and determining an accommodative amplitude of the lens in the eye of the subject based on the distance so determined. The movement of the target may be controlled by the subject viewing the target, and may be controlled by the subject without assistance from another person. The subject may control the movement of the target by using one or more of the controllers described hereinabove. The method may also include a step of illuminating an image provided on the target that is opaque and occupies a minor portion of the area of the target.

When the methods are used to measure accommodation of accommodating intraocular lenses implanted in an eye, the results may be used to determine if the accommodative amplitude is sufficient to improve the vision of the subject. In addition, the method may be practiced to compare accommodative abilities of different intraocular lenses, and thereby provide the ability to select the best fit intraocular lens for a particular patient.

Apparatus 10 also includes an instrumentation aperture 28, which permits one or more additional ophthalmic instruments to be connected to apparatus 10. Instrumentation aperture 28 is shown as being located on the opposite side of housing 12 with respect to viewing aperture 20. Because mirror 30 is positioned between viewing aperture 20 and instrumentation aperture 28, it is preferable to use a "cold mirror" which allows infrared energy to pass through the mirror. Accordingly, apparatus 10 may also include an ophthalmic instrument positioned so that infrared energy may be emitted from the ophthalmic instrument and pass through instrumentation aperture 28 to the subject's eye. The use of infrared energy permits additional measurements of the subject's eye without interfering with the subject's visual test of viewing the target in apparatus 10. Examples of ophthalmic instruments include, and are not limited to, power refractors, and partial coherence interferometers.

In one specific embodiment of apparatus 10, which is provided only by way of example, and not by way of limitation, the length of housing 12 is approximately 385 mm, the width is approximately 60 mm, and the height of housing 12 is approximately 60 mm. The target 32 within such a housing is approximately 40 mm wide by 40 mm high. The housing 12 is positioned with respect to an eye of a subject so that the optical axis of lens 42 is about 105 mm from the subject's eye, and the viewing aperture 20 is about 65 mm from the subject's eye. The Badal lens has about a 160 mm focal length, and the lens is positioned about 160 mm (or one focal length) away from mirror 30. In this apparatus, some settings may include a high diopter setting of +5.5 diopters, a low diopter setting of −0.5 diopters, a scan speed of about 0.30 diopters per second, a brightness level of 6, and an offset of 0.0 diopters.

While this invention has been described with respect to various specific examples and embodiments, it is to be understood that the invention is not limited thereto and other embodiments are within the scope of the invention.

What is claimed is:

1. Apparatus for measuring accommodation of a lens in an eye of a subject, consisting essentially of:
    a housing;
    a viewing target located in the housing on a track that permits the viewing target to move in the housing;
    a viewing aperture located in the housing to permit the subject to view the viewing target;
    a single Badal lens located between the viewing target and the viewing aperture at a position that provides a substantially constant apparent size of the viewing target when viewed by the subject regardless of the distance between the viewing target and the aperture; and
    a computer operatively coupled to the viewing target and programmed to monitor a distance over which the viewing target moves and to calculate an accommodation amplitude based on the measured distance.

2. The apparatus of claim 1, wherein the viewing target is a physical target.

3. The apparatus of claim 1, wherein the viewing target includes an image provided on a slide.

4. The apparatus of claim 1, further consisting essentially of an illumination source to illuminate the viewing target.

5. The apparatus of claim 4, wherein the illumination source is movable with the viewing target.

6. The apparatus of claim 4, wherein the viewing target includes an image located between the illumination source and the lens, and a light transmitting background member located in proximity to the image.

7. The apparatus of claim 6, wherein the background member is located between the illumination source and the image.

8. The apparatus of claim 1, wherein the track includes a plurality of increments to permit the viewing target to incrementally move along the track.

9. The apparatus of claim 1, further consisting essentially of a drive mechanism in communication with the viewing target and the track to control the movement of the viewing target along the track.

10. The apparatus of claim 1, wherein the viewing apparatus is located near one end of the housing.

11. The apparatus of claim 1, further consisting essentially of a mirror located between the viewing aperture and the lens so that the viewing target may be viewed by the subject when the viewing aperture is provided in the housing at a location that is not along an optical axis of the lens.

12. The apparatus of claim 1, wherein the viewing target includes an image disposed on a light colored background member.

13. The apparatus of claim 12, wherein the image and the light colored background member are dimensioned to maintain a relatively constant pupil size of the subject the subject is viewing the viewing target as the viewing target moves in the housing.

14. The apparatus of claim 1, further consisting essentially of a controller operatively coupled to the viewing target to control movement of the viewing target along the track.

15. The apparatus of claim 14, wherein the controller is dimensioned to be held by, the subject viewing the viewing target.

16. The apparatus of claim 1, wherein the computer operatively coupled to the viewing target is programmed to determine the amount of accommodation of the lens in the eye of the subject.

17. Apparatus for measuring accommodation of a lens in an eye of a subject, comprising:
    a housing;
    a viewing target located in the housing on a track that permits the target to move in the housing;
    a viewing aperture located in the housing to permit the subject to view the viewing target; and
    a lens located between the viewing target and the viewing aperture at a position that provides a substantially constant apparent size of the viewing target when viewed by the subject regardless of the distance between the viewing target and the aperture; and
    at least one controller coupled to the viewing target to control movement of the viewing target along the track, and said control configured to control a rate at which the viewing target moves along the track, and to control a brightness of the viewing target.

18. Apparatus for measuring accommodation of a lens in eye of a subject, comprising:
    a housing;
    a viewing target located in the housing on a track that permits the viewing target to move in the housing;
    a viewing aperture located in the housing to permit the subject to view the viewing target; and
    a lens located between the viewing target and the viewing aperture at a position that provides a substantially constant apparent size of the viewing target when viewed by the subject regardless of the distance between the viewing target and the aperture; and
    at least one controller coupled to the viewing target to control movement of the viewing target along the track, and said controller includes a computer to determine the distance the viewing target moves along the track.

19. Apparatus for measuring accommodation of a lens in the eye of a subject, comprising:
    a viewing aperture;
    a physical target positioned on a track so that the physical target can move along the track toward or away from an eye of a subject viewing the physical target through the viewing aperture;

a lens located in the apparatus so that when the physical target is viewed by the subject through the viewing aperture, the lens is positioned between the physical target and the subject's eye, and the physical target has a substantially constant apparent size regardless of the distance between the physical target and the viewing aperture; and a computer operatively coupled to the physical target and programmed to monitor a distance over which the physical target moves and to calculate an accommodation amplitude based on the measured distance.

20. The apparatus of claim 19, which further comprises an illumination source to illuminate the physical target.

21. The apparatus of claim 20, wherein the physical target comprises an image having an opaque region and a transparent region, and the illumination source is positioned so that light provided by the illumination source passes through the transparent region.

22. The apparatus of claim 20, wherein the physical target further comprises a translucent member disposed between the illumination source and the image.

23. The apparatus of claim 19, further comprising a mirror located in the apparatus and positioned so that the subject may view the physical target without being located along a central axis of the lens.

24. The apparatus of claim 23, wherein the mirror is positioned so that the subject may view the physical target when positioned at an approximately ninety degree angle to the central optical axis of the lens.

25. The apparatus of claim 19, further comprising a controller operatively coupled to the physical target to control movement of the physical target along the track.

26. Apparatus for measuring accommodation of a lens in the eye of a subject, comprising:

a target located in the apparatus and moveable toward or away from the eye of the subject when the subject is viewing the target, the target being structured to maintain substantially constant pupil size of the eye as the target is moved toward or away from the eye; and a computer operatively coupled to the target that is programmed to determine the accommodation of a lens in the eye of the subject by monitoring the distance the target moves when viewed by the subject, and calculating an accommodation amplitude based on the distance.

27. The apparatus of claim 26, further comprising a lens disposed between the target and the eye of the subject when the subject is viewing the target, the lens being structured to maintain a substantially constant apparent size of the target as the target moves within the apparatus while being viewed by the subject.

28. A method for measuring and comparing accommodation of a plurality of intraocular lens implanted in an eye of a subject, the method comprising the steps of:

a) moving a target, which is structured to maintain a relatively constant pupil size in the eye of the subject viewing the target, from a first position towards or away from the subject's eye to a second position;

b) determining the distance between the first position and the second position;

c) determining the accommodative abilities of a first of the plurality of intraocular lens implanted in the eye of the subject based on the distance determined in step (b);

d) repeating steps (a)–(c) for a second of the plurality of intraocular lens, and wherein the first and second of the plurality of intraocular lens are implanted at separate times into the eye.

* * * * *